United States Patent [19]

Cummins

[11] Patent Number: 4,497,795

[45] Date of Patent: Feb. 5, 1985

[54] METHOD OF REGULATING APPETITE AND EFFICIENCY OF FOOD UTILIZATION EMPLOYING INTERFERON

[75] Inventor: Joseph M. Cummins, Amarillo, Tex.

[73] Assignee: The Texas A&M University System, College Station, Tex.

[21] Appl. No.: 448,951

[22] Filed: Dec. 13, 1982

[51] Int. Cl.³ .............................................. A61K 45/02
[52] U.S. Cl. ....................................... 424/85; 435/811
[58] Field of Search ...................... 424/85; 260/112 R; 435/68, 811

[56] References Cited

PUBLICATIONS

Marx, *Science*, 210, 998, (1980).

*Journal of Infectious Diseases*, 139, 109–23, (1979).

Primary Examiner—Blondel Hazel
Attorney, Agent, or Firm—Arnold, White & Durkee

[57] ABSTRACT

The appetite of a warm-blooded vertebrate can be regulated by administering to the vertebrate a biological active fraction of interferon in an amount effective to modulate the vertebrate's food intake or efficiency in utilizing food. The appetite of a cow can be stimulated by the oral or intravenous administration of bovine fibroblast interferon or by interferon secreted nasally by the cow in response to inoculation with a vaccinal virus strain such as that of infectious bovine rhinotracheitis virus. The appetite of swine can be enhanced by oral administration of bovine fibroblast interferon.

18 Claims, No Drawings

METHOD OF REGULATING APPETITE AND EFFICIENCY OF FOOD UTILIZATION EMPLOYING INTERFERON

BACKGROUND OF THE INVENTION

This invention relates generally to a novel method for regulating the appetite of warm-blooded vertebrates. More particularly, this invention concerns the use of interferon isolates to modulate the appetite and increase the efficiency of food utilization for animals such as cattle, swine, and chickens.

"Interferon" is a term generically comprehending a group of vertebrate glycoproteins and proteins which are known to have various biological activities, such as antiviral, antiproliferative, and immunomodulatory activity in the species of animal from which such substances are derived. The following definition for interferon has been accepted by an international committee assembled to devise a system for the orderly nomenclature of interferons: "To qualify as an interferon a factor must be a protein which exerts virus nonspecific, antiviral activity at least in homologous cells through cellular metabolic processes involving synthesis of both RNA and protein." *Journal of Interferon Research*, 1, pp. vi (1980).

Since the first descriptions of interferon by Isaacs and Lindeman [See, Proc. Roy. Soc. London (Ser.B), Vol. 147, pp. 258 et seq. (1957) and U.S. Pat. No. 3,699,222], interferon has been the subject of intensive research on a worldwide basis. Publications abound concerning the synthesis of interferon, its proposed molecular characterizations, its clinical applications, and proposed mechanisms of its antitumor, antiviral, and immune system activities. See, for example, DeMaeyer, et al., "Interferons" appearing as Chapter 5 in *Comparative Virology*, Vol. 15, pp. 205–284, Plenum Press, N.Y., N.Y. (1979); Cantrell, "Why Is Interferon Not In Clinical Use Today" appearing in *Interferon* 1979, I. Gresser, ed., Vol. 1, pp. 1–28, Academic Press, London (1979); Stewart, "The Interferon System" Springer-Verlag, N.Y., N.Y. (1979); and Dunnick, et al., "Clinical Trials with Exogenous Interferon", *J. Infect. Diseases*, 139, No. 1, pp. 109–123 (1979).

Because of the intensity and disparate origins of research concerning interferon and its characteristics and uses, there exists a substantial lack of uniformity in such matters as classification of interferon types. There are also numerous, sometimes contradictory, theories concerning the mode of action of interferon in producing clinical effects. The following brief summary of the current state of knowledge regarding interferon will aid in understanding the present invention.

Although originally isolated from cells of avian origin (chick allantoic cells), interferon production has been observed in cells of all classes of vertebrates, including mammals, amphibians, and reptiles. Interferon production by vertebrate cells is seldom spontaneous but is often readily "induced" by treatment of cells (in vivo or in vitro) with a variety of substances including viruses, nucleic acids (including those of viral origin as well as synthetic polynucleotides), lipopolysaccharides, and various antigens and mitogens.

Interferon have generally been named in terms of the species of animal cells producing the substance (e.g., human, murine, or bovine), the type of cell involved (e.g., leukocyte, lymphoblastoid, fibroblast) and, occassionally, the type of inducing material responsible for interferon production (e.g., virus, immune). Interferon has been loosely classified by some researchers according to induction mode as either Type I or Type II, with the former classification comprehending viral and nucleic acid induced interferon and the latter class including the material produced as a lymphokine through induction by antigens and mitogens. More recently, the international committee devising an orderly nomenclature system for intereferon has classified interferon into types on the basis of antigenic specificities. In this newer classification, the designations alpha ($\alpha$), beta ($\beta$), and gamma ($\gamma$) have been used to correspond to previous designations of leukocyts, fibroblast, and type II (immune) interferons, respectively. Alpha and beta interferons are usually acid-stable and correspond to what have been called type I interferons; gamma intereferons are usually acid-labile and correspond to what has been called type II intereferons. The international committee's nomenclature recommendations apply only to human and murine interferons. *Journal of Interferon Research*, 1, pp. vi (1980). Therefore, the interferon employed herein is identified simply by animal species and type of cell producing the intereferon, e.g. bovine fibroblast interferon.

Determination of precise molecular structures for interferon was for some time beyond the capacities of the art. In the years since interferon was first characterized as proteinaceous on grounds of its inactivation by trypsin, attempts to purify and uniquely characterize it have been frustrated by its high specific activity as well as its apparent heterogeneity. Presently, some precision in determining molecular structure has been achieved for interferon derived from a single cell type and using a single specific inducer, e.g., human alpha interferon.

In its earliest applications, interferon was employed exclusively as an antiviral agent and the most successful clinical therapeutic applications to date have been in the treatment of viral or virus-related disease states. It became apparent, however, that exogenous interferon was sometimes capable of effecting regression or remission of various metastatic diseases. A summary of clinical trials of interferon as an antiviral and antiproliferative therapeutic agent through late 1978 is contained in Dunnick, et al. supra.

The clinical agent of choice in this work has been human leukocyte interferon, "mass-produced" by procedures involving collection and purification of vast quantities of human buffy cost leukocytes, induction with virus, and isolation from culture media. The need for interferon of human source is, of course, consistent with the long-standing conclusion that interferon is "species specific", i.e., biologically active, in vivo, only in species homologous to the source cells.

In the work described above, interferon has been administered parenterally, i.e., intramuscularly and intradermally, with some successful topical usages having been reported. It has seldom been administered intravenously because of substantial adverse effects attributable to "contaminants" in crude and even highly purified isolates. Prior to applicant's invention described in U.S. patent application, Ser. No. 180,464, filed Aug. 22, 1980, and in PCT International Application No. PCT/US 81/01103, filed Aug. 18, 1981, published Mar. 4, 1982, the disclosures of which are hereby incorporated by reference, there had been no reports of therapeutically successful oral administration of interferon. This circumstance was consistent with the widely held belief that interferon would not withstand exposure to a digestive environment such as that found in mammals.

In addition to use in antiviral and antitumor therapy, interferon has rather recently been noted to possess immunomodulatory effects, both immunopotentiating and immunosuppressive in nature. See, e.g., Sonnenfeld, et al., "A Regulatory Role For Interferon In Immunity", Annals, N.Y. Acad. Sci., Vol. 322, pp. 345-355 (1979). While no human clinical or in vivo animal work specifically directed to evaluation of immunological effects of interferon has been reported, it is proposed by some that the antitumor effects of interferon are at least in part related to immune stimulation or activation of so-called "natural killer cells," macrophages and T-lymphocytes. See, e.g., Kershner, "New Directions in Cancer Chemoherapty" *A.S.M.News*, Vol. 46, No. 3, pp. 102 et seq. (1980).

Further, "new" biological activities for exogenous interferon are consistently being ascertained. Cantrell, et al., *New Eng. Jour. Med.*, Vol. 302, No. 18, P. 1032 (1980) report an effect of interferon in transiently diminishing high density lipoprotein levels and total cholesterol values, suggesting that interferon in humans, may influence cardiovascular disease.

Prior to applicant's invention described and claimed in the present application, there had been no reports of any biological activity of any form of interferon with a direct impact upon the appetite or efficiency of food utilization in vertebrates. Insofar as the possibility of using interferon to stimulate appetite is concerned, interferon has been considered in the art as possessing the opposite effect. It has been reported in the literature that human patients receiving interferon cancer therapy experience a loss of appetite as a side effect of such therapy. Marx, Science 210, p. 998 (1980); *Journal of Infectious Diseases*, 139, pp. 109-25 (1979). This suppression of appetite has been one of a number of side effects, such as lower white blood cell counts, nausea, fever, and hair loss, experienced by humans in clinical trials of interferon. Further, the prior art literature has not reported any effect of interferon upon appetite in nonhuman species.

SUMMARY OF THE INVENTION

According to the present invention, it has been discovered that the appetite of a warm-blooded vertebrate can be regulated by a method comprising administering to the warm-blooded vertebrate a biologically active fraction of interferon in an amount effective to modulate the vertebrate's food intake or efficiency in utilizing food. The amounts of interferon effective to modulate food intake have been discovered to be much lower than those amounts of interferon necessary to realize its antiviral, antitumor, and modulatory effects. Though the exact mechanism by which interferon affects appetite remains unconfirmed, applicant believes that he has discovered an effect of interferon upon the satiety center and hunger centers of the brain and central nervous system, rather than a mere side effect or toxic effect realized from administration of interferon. This method of regulating appetite is presently believed to be of the most value in stimulating the appetite of mammals but also finds application in modulation of the food intake or efficiency of food utilization of any warm-blooded vertebrates, including avian species.

Interferon derived from any cell source may be used in the method of the present invention. Genetically engineered interferon may also be used. Fibroblast interferon found in cells of bovine species origin is the presently preferred type of interferon, principally because of its easy availability in relatively large quantities.

In the method for stimulating the appetite of cattle which also forms part of the present invention, cattle are orally administered a biologically active fraction of fibroblast interferon derived from cells of bovine species origin. When orally administered, cattle should receive at least one dose of at least 10,000 units of such interferon per kg of body weight.

Though oral administration of the bovine fibroblast interferon is preferred, the appetite of cattle may also be stimulated by intravenous administration of the bovine fibroblast interferon. When intravenously administered, each bovine should be given daily for at least three days at least one dose of about 4,000 units of such interferon per kg of body weight.

Though bovine fibroblast interferon is preferred for use in stimulating the appetite of cattle, the interferon may also be secreted nasally by the cattle in response to innoculation with a vaccinal virus strain, such as that of infectious bovine rhinotracheitis (IBR) virus. Each bovine may be innoculated with at least about $10^4$ TCID$_{50}$ of such vaccinal strain.

Also forming a part of the present invention is a method for stimulating the appetite of swine comprising administration of a biologically active fraction of interferon. At present, this method of stimulating the appetite of swine entails the oral administration of bovine fibroblast interferon to piglets prior to weaning. Preferably, each pig is given from about 5,000 to about 50,000 units per kg of body weight of such interferon per day for one to five days before weaning.

A method for increasing the efficiency of food utilization in chickens also forms a part of the present invention. This method comprises administering a biologically active fraction of interferon glycoprotein, the preferred interferon being bovine fibroblast interferon. Preferably, the chickens receive the bovine fibroblast interferon in their drinking water, in an amount at least about 70 units per ml of drinking water.

Examples of the more important features of this invention have thus been summarized rather broadly in order that the detailed description thereof that follows may be better understood, and in order that the contribution to the art may be better appreciated. There are, of course, additional features of the invention that will be described hereinafter and which will also form the subject of the claims appended thereto.

DETAILED DESCRIPTION OF THE PREFERRED EMBODIMENTS

As employed throughout this application, the term "interferon" shall have the meaning ordinarily attributed thereto in the art, including but not limited to the meaning ascribed thereto in U.S. Pat. No. 3,699,222.

Interferon of human and murine origins has been quantified in the art in terms of International Units ("IU"), notwithstanding knowledge that, for example, the molecular weight of human leukocyte and lymphoblastoid ranges between 13,000 and 25,000 daltons. As used herein, a "unit" of interferon shall mean the reciprocal of a dilution of interferon-containing material that, as determined by assay, inhibits one-half of a challenge virus plaque, the challenge virus being the vesicular stomatitis virus (VSV).

Unless otherwise indicated, as used throughout the examples presented herein, "bovine fibroblast interferon, "bovine IFN," or "IFN" shall means that interferon which has been prepared in accord with the procedures of Example 1.

EXAMPLE 1

Primary bovine fetal kidney (BFK) or bovine testicular (BT) cells were grown to confluency in cell culture. Stocks of bluetongue virus (international serotype 10) were prepared in baby hamster kidney (BHK) cells or VERO cells and had titers of $10^6$ to $10^8$ plaque forming units (PFU)/ml. The BFK or BT cells were challenged with bluetongue virus (multiplicity of infection of greater than 1 was best), and supernatant fluids were generally harvested when the cytopathic effect (CPE) involved the entire cell sheet, i.e., about 24 to 48 hours. The supernatant fluids were dialyzed for 24 hours in a KCl-HCl buffer (ph 2.0) and for 24 hours in a phosphate buffered saline (ph 7.4) before ultracentrifugation at $100,000 \times g$ for 60 minutes. The interferon activity (expressed as "units" as opposed to IU) was assayed by a plaque reduction method using VSV as a challenge virus on BFK cells Rosenquist and Loan, "Interferon Production With Strain SF-4 of Parainfluenza-3 Virus" *Am. J. Vet. Res.,* 28, pp. 619–628 (1967).

While phosphate buffered saline was used as a carrier for interferon, other pharmaceutically acceptable diluents, adjuvants, and carriers of the type commonly used in oral and parenteral therapy must be employed.

EXAMPLE 2

A set of healthy guinea pigs, already consuming near maximum amounts of food, were used to test the bovine fibroblast interferon of Example 1 for toxicity. Each animal was orally administered the amount of bovine IFN indicated in Table A. The particular IFN preparation given in this study had a titer of 3000 units/ml. As indicated in Table A, those guinea pigs given IFN gained an average of 30 grams each, while the controls lost an average of 20 grams.

TABLE A

Guinea Pigs Administered Oral IFN or Placebo for Seven Days

| Animal No. | Treatment Group | Starting Weight (gms) | Finishing* Weight (gms) | Net Change (gms) |
|---|---|---|---|---|
| 1 | Control | 475.4 | 457.4 | −18.0 |
| 2 | Control | 429.5 | 407.2 | −22.3 |
| | | 904.9 | 864.6 | −40.3 |
| 3 | IFN Once Daily (2 ml/day) | 450.0 | 493.8 | +43.8 |
| 4 | IFN Once Daily (2 ml/day) | 378.6 | 432.8 | +54.2 |
| | | 828.6 | 926.6 | +98.0 |
| 5 | IFN Twice Daily (4 ml/day) | 428.3 | 419.7 | −8.6 |
| 6 | IFM Twice Daily (4 ml/day) | 432.7 | 465.0 | +32.3 |
| | | 861.0 | 884.7 | +23.7 |
| Total | All Animals | 2,594.5 | 2,675.9 | +81.4 |
| Average | All Animals | 432.425 | 445.983 | +13.558 |
| Average | IFM Only | 422.400 | 452.825 | +30.425 |
| Average | Controls Only | 452.450 | 432.300 | −20.150 |

*Finishing weight taken 10 days after starting weight.

EXAMPLE 3

In another trail involving guinea pigs, ten pigs were used as controls against eight pigs that were orally administered 1 cc/day of a bovine IFN preparation having a titer of 8000 units/ml. The data from this study are summarized in Table B. Bovine IFN was administered for five days only, and all guinea pigs were observed for ten days more. During the first five days of treatment, each group was consuming nearly the same amounts of food, but the IFN-treated guinea pigs ate 8.1% more after treatment, and the controls ate 1.2% less.

TABLE B

Daily Food Consumption (Grams) per Guinea Pig per Group - IFN Administered vs. Controls

| Period | Group (No.) IFN (8) | Controls (10) |
|---|---|---|
| 1st 5 days | 38.2 | 38.4 |
| 2nd 5 days | 40.0 | 37.6 |
| 3rd 5 days | 41.3 | 38.0 |
| Change (%): | | |
| 1st 5-2nd 5 | +4.7 | −2.2 |
| 1st 5-3rd 5 | +8.1 | −1.2 |

EXAMPLE 4

Male broiler chickens were tested for two weeks to provide data on the effect of bovine IFN on efficiency of feed utilization and feed consumption in chickens. This study involved four groups of sixteen baby chicks each, one group being a control. The baby chicks were given bovine IFN in their drinking water at dilutions of 1:10, 1:100, and 1:1000, respectively, of a bovine IFN preparation having a titer of 7000 units/ml. As shown in Table C, the group of chicks receiving the 1:10 IFN dilution gave a favorable response. The groups of chicks all had nearly the same average finishing weight, but those treated with the 1:10 IFN dilution were 10.4% more efficient, requiring less food for a pound of weight gain.

TABLE C

Effect of Interferon on Efficiency of Feed Utilization and Feed Consumption in Male Broiler Chicks

| Water Treatment (IFN units/ml) | Avg. wt. (gm) | Lb feed/ Lb gain | Feed consumed/ bird (gm) | $H_2O$ consumed/ bird (mls) |
|---|---|---|---|---|
| 0 | 194.0 | 1.54 | 299 | 456 |
| 700 | 194.5 | 1.38 | 268 | 496 |
| 70 | 194.8 | 1.60 | 312 | 436 |
| 7 | 192.3 | 1.53 | 293 | 439 |

EXAMPLE 5

In another study of the effect of bovine IFN on broiler chicks, forty male broiler chicks were tested, twenty treated with IFN and twenty acting as a control group. The IFN-treated chicks had 700 units of IFN per ml added to their normal drinking water for two weeks. All chicks were observed and their weight gain monitored for eight weeks. As shown in Table D feed consumption was adversely affected at the particular IFN dosage under study.

The effect of IFN observed in examples 4 and 5 will be useful in preventing excessive weight gain in breeding flocks of the poultry industry. The appropriate dose of IFN will result in less feed consumption but increased efficiency in utilizing feed, resulting in less fat and more protein deposition.

TABLE D

Interferon Effect on Broiler Chicks When Supplied Via the Drinking Water

| Treatment | Weights (gms) | | | | | | | | Total ml H$_2$O | Feed Efficiency |
|---|---|---|---|---|---|---|---|---|---|---|
| Week | 1 | 2 | 3 | 4 | 5 | 6 | 7 | 8 | 0-4 wks | 0-8 wks |
| IFN-Treated | 106.5 | 237.9 | 334.9 | 553.9 | 867.4 | 1106.8 | 1442.9 | 1533.5 | 1193.0 | 2.47 |
| Control | 105.8 | 243.4 | 358.1 | 569.4 | 915.6 | 1211.3 | 1537.2 | 1656.4 | 1221.7 | 2.30 |

EXAMPLE 6

A collection of calves, all suffering from severe illness and accompanying anorexia, were used to study the effects of orally administered bovine IFN. Ten of the calves acted as controls, and three of the calves were orally administered a single dose of 90 ml of a bovine IFN preparation with a titer of 7000 units/ml. As shown in Table E, the calves' total feed consumption for 4 days (Day 2-Day 5) prior to IFN administration was only 0.3-1.6 lbs., recorded by the pinpointer. A 400-lb calf normally eats 1% of its body weight the first week in the feedlot, and 2% the second week. Thus, all calves used in this study were exhibiting severe appetite suppression. Within two days of the single IFN treatment, the IFN-treated calves were all eating five pounds of feed or more, while only one of the ten controls was eating that much. All three IFN-treated calves survived the study, while only four of the ten controls survived.

EXAMPLE 7

A test was conducted to study the effect of bovine IFN on Pasteurella-vaccinated calves. Thirty-seven (37) calves were intradermally vaccinated with 0.5 ml of A. H. Robins' Pasteurella vaccine (live Pasteurella hemolytica, serotype 1), while 45 were given a placebo injection. At least 20 days after the vaccinations, 24 of the unvaccinated calves and 18 of the vaccinated were each administered a single oral dose of bovine IFN with a titer of 7000 units/ml. The remaining calves were each given a placebo. Each IFN-treated calf received 120 ml of the IFN if it weighed more than 400 lbs or 90 ml of the IFN if it weighed less than 400 lbs. The food consumption and weight gain averaged for each group at seven days after treatment with IFN are reported in Table F. Vaccinated calves given IFN ate 40% more the first week thereafter than vaccinated calves given a placebo. Unvaccinated calves given a placebo ate 13% more the first week thereafter than unvaccinated calves given IFN. The different response between vaccinates and controls may have been due to some interaction between IFN treatment and vaccination that may have produced more severe appetite suppression in vaccinates. Also, the comparison between IFN-treated and control calves had more validity for the vaccinated calves because the average weights of the IFN-treated and control calves were much closer than for the unvaccinated calves. In the unvaccinated group, the controls were heavier than the IFN-treated calves, and thus probably older and more likely to perform better.

TABLE E

Daily Consumption of Food by Sick Cattle

| Calf No. | 2-5* | 6** | 7 | 8 | 9 | 10 | 11 | 12 | Fate 2 Months After Test Commenced |
|---|---|---|---|---|---|---|---|---|---|
| Controls | | | | | | | | | |
| 63 | 0.3 | 0 | 0 | 0 | | | Dead | | Died |
| 77 | 1.6 | 0 | 0 | 0 | 0 | 0 | Pulled | | Survived |
| 85 | 1.2 | 0 | 0 | 0 | 0 | 0 | Pulled | | Died |
| 91 | 0.8 | 0 | 0 | 0 | 0 | 0 | Dead | | Died |
| 143 | 0.9 | 0.3 | 2.2 | 5.6 | 9.8 | 8.3 | 9.2 | 8.7 | Survived |
| 191 | 0.3 | 0 | 0 | 0 | 0 | 2.3 | 2.7 | Pulled | Survived |
| 254 | 0.7 | 0 | 0.6 | 0 | 0 | 0 | Pulled | Dead | Died |
| 290 | 0.3 | 0 | 0 | 0 | | | Dead | | Died |
| 299 | 0.7 | 0 | 0 | 0 | 1.3 | 4.5 | 5.6 | 8.6 | Survived |
| 375 | 0.4 | 0 | 0 | 0 | 0 | 0.7 | Pulled | Dead | Died |
| IFN Treated | | | | | | | | | |
| 44 | 0.8 | 0.4 | 1.1 | 5.0 | 10.2 | 5.0 | 5.6 | 10.9 | Survived |
| 112 | 0.3 | 0 | 4.1 | 10.2 | 9.6 | 14.7 | 16.1 | 15.4 | Survived |
| 173 | 1.2 | 0.4 | 2.4 | 5.3 | 6.2 | 2.5 | 1.3 | 2.8 | Survived |

Numbers under days represents pounds of food consumed that day.
"Pulled" means the calf was treated for illness and removed from the pinpointer.
*Total pounds of food consumed on days 2-5.
**IFN administered on the morning of the 6th day.

TABLE F

Effect of Oral IFN Treated on Pasteurella-Vaccinated Calves - 7-Day Data on 82 Calves Consuming Food as Determined by Pinpointer

| Group | No. of Calves | Average Weight | Group Weight | 7-Day Consumption | Avg. Daily Consumption | % of Avg. Wt. Consumed Daily |
|---|---|---|---|---|---|---|
| Unvaccinated No IFN | 24 | 420.2 | 10,086 | 1,041.6 | 6.2 | 1.50 |
| Unvaccinated IFN | 21 | 391.8 | 8,228 | 761.1 | 5.2 | 1.33 |
| Vaccinated IFN | 18 | 412.4 | 7,424 | 832.8 | 6.6 | 1.63 |
| Vaccinated No IFN | 19 | 407.1 | 7,734 | 623.3 | 4.7 | 1.16 |

EXAMPLE 8

Two calves that were consuming an average of 14.6 lbs of feed per day for four days were intravenously given 800,000 units of bovine IFN on each of four days (Days 0, 1, 2, and 3 of Table G). On each day of the IFN treatment, each calf consumed less than 14.5 lbs, even dropping as low as 6.5 and 6.7 lbs respectively on the last day of treatment. After completion of the IFN treatment itself, feed consumption for both calves increased substantially.

TABLE G

Feed Consumption (lbs) by Calves Given Bovine IFN Intravenously

| Calf No. | Day After Intravenous Inoculation | | | | | | | | | | | |
|---|---|---|---|---|---|---|---|---|---|---|---|---|
| | 0 | 1 | 2 | 3 | 4 | 5 | 6 | 7 | 8 | 9 | 10 | 11 |
| 461 | 13.0 | 11.1 | 13.8 | 6.5 | 17.4 | 23.3 | 22.4 | 17.7 | 23.4 | 19.6 | 21.9 | 27.8 |
| 490 | 13.4 | 12.0 | 12.3 | 6.7 | 16.4 | 14.0 | 21.5 | 17.5 | 15.4 | 17.6 | 20.9 | 18.7 |

TABLE H

| Vaccine | IBR/PI-3 Vaccine Dosages (Virus Liters) Product Information (Virus Liters) |
|---|---|
| Anchor Labs (IM) | IBR $\geq 10^{5.5}$TCID$_{50}$; PI-3 $\geq 10^{5.8}$TCID$_{50}$ |
| TSV-2 | IBR$_{TS}$ = $10^{5.5}$TCID$_{50}$; PI-3$_{TS}$ = $10^{6.4}$TCID$_{50}$ |
| Rhivin | IBR = $10^{6.1}$TCID$_{50}$; PI-3 = $10^{7.1}$TCID$_{50}$ |
| Rhivin/10 | IBR = $10^{5.1}$TCID$_{50}$; PI-3 = $10^{6.1}$TCID$_{50}$ |

TABLE I

Food Consumption (lbs) by Calves After Vaccination with Intranasally Administered IBR and PI-3 Vaccine (TSV-2)

| Calf No. | Days After Vaccination | | |
|---|---|---|---|
| | 1-14 | 15-28 | 1-28 |
| Controls: | | | |
| 5 | 219 | 282 | 501 |
| 8 | 191 | 161 | 352 |
| 9 | 116 | 160 | 276 |
| 22 | 283 | 267 | 550 |
| 40 | 172 | 207 | 379 |
| 41 | 225 | 254 | 479 |
| 88 | 163 | 170 | 333 |
| 91 | 227 | 283 | 510 |
| Total | 1,596 | 1,784 | 3,380 |
| Average | 200 | 223 | 423 |
| Daily Average | 14.3 | 15.9 | 15.1 |
| Vaccinates: | | | |
| 1 | 273 | 273 | 546 |
| 10 | 272 | 415 | 687 |
| 12 | 114 | 154 | 268 |
| 50 | 180 | 146 | 326 |
| 79 | 199 | 230 | 429 |
| 82 | 132 | 189 | 321 |
| 85 | 221 | 294 | 515 |
| 93 | 219 | 305 | 524 |
| Total | 1,610 | 2,006 | 3,616 |
| Average | 201 | 251 | 452 |
| Daily Average | 14.4 | 17.9 | 16.1 |

EXAMPLE 9

In this study, the source of interferon was nasal secretions induced by vaccination with a vaccine (TSV-2) prepared from temperature sensitive mutant of infectious bovine rhinotracheitis (IBR) virus and parainfluenza-3 (PI-3) virus. The temperature sensitive strain of attenuated IBR virus was prepared by Norden Laboratories of Lincoln, Nebr. Materials and methods used in preparing the temperature sensitive strain of IBR virus are described in more detail in "Evaluation of the Safety and Efficacy of an Intranasal Vaccine Containing a Temperature-Sensitive Strain of Infectious Bovine Rhinotracheitis Virus", Kucera et al, Am J Vet Res, 39, 607–10 (1978). The TSV-2 vaccine also contains a temperature sensitive strain of PI-3. Temperature sensitivity means that the viruses are treated so that they cannot replicate at the body temperature of the cow and their growth is restricted to the nasal mucosa. Eight calves were given TSV-2, and eight calves were treated as controls. One ml of the TSV-2 vaccine containing about 300,000 TCID$_{50}$ of IBR virus was administered to each nostril of each treated calf. The complete virus titers for the TSV-2 vaccine administered in the amount recommended by Norden Laboratories is shown in Table H. After vaccination, each calf was monitored to record weight gain and its daily feed consumption determined by pinpointer. Table I reports the feed consumption data for each calf and shows the vaccinated calves consumed more food than the unvaccinated controls. Table J reports the body weight data and shows that the vaccinated calves gained more weight and did so more efficiently than the unvaccinated controls.

TABLE J

Body Weights of Calves Following Vaccination with Intranasally Administered IB and PI-3 Vaccine (TSV-2)

| Calf No. | Days After Vaccination | | | Gain, 1-28 |
|---|---|---|---|---|
| | 0 | 14 | 28 | |
| Controls: | | | | |

TABLE J-continued
Body Weights of Calves Following Vaccination with Intranasally Administered IB and PI-3 Vaccine (TSV-2)

| Calf No. | Days After Vaccination | | | Gain, 1-28 |
|---|---|---|---|---|
| | 0 | 14 | 28 | |
| 5 | 660 | 664 | 752 | 92 |
| 8 | 526 | 546 | 606 | 80 |
| 9 | 410 | 384 | 442 | 32 |
| 22 | 658 | 690 | 758 | 100 |
| 40 | 456 | 460 | 510 | 54 |
| 41 | 526 | 544 | 604 | 78 |
| 88 | 498 | 540 | 562 | 64 |
| 91 | 474 | 472 | 546 | 72 |
| Total | 4,208 | 4,300 | 4,780 | 572 |
| Average | 526 | 537.5 | 597.5 | 71.5 |
| Average Daily Gain | — | 0.82 | 4.29 | 2.55 |
| Vaccinates: | | | | |
| 1 | 636 | 688 | 752 | 116 |
| 10 | 528 | 540 | 636 | 108 |
| 12 | 426 | 440 | 496 | 70 |
| 50 | 444 | 474 | 528 | 84 |
| 79 | 568 | 560 | 642 | 74 |
| 82 | 478 | 510 | 570 | 92 |
| 85 | 654 | 662 | 754 | 100 |
| 93 | 434 | 428 | 492 | 58 |
| Total | 4,168 | 4,302 | 4,870 | 702 |
| Average | 521 | 537.8 | 608.8 | 87.8 |
| Average Daily Gain | — | 1.20 | 5.07 | 3.13 |

The presence of interferon in the nasal secretions of each calf in the study was monitored for ten days after vaccination by intranasal administration of the TSV-2 vaccine. As shown in Table K, during the ten days after vaccination, IFN was detected in 56 of 76 (74%) and in 2 of 63 (3%) of nasal secretion samples collected from vaccinates and controls, respectively. From 3 through 8 days after vaccination, IFN was detected in 51 of 55 (93%) samples collected from vaccinates.

TABLE K
Interferon Titers in the Nasal Secretions of Calves After Intranasal Administration of IBR Vaccine (TSV-2)

| Calf No. | Day After Intravenous Inoculation | | | | | | | | | | |
|---|---|---|---|---|---|---|---|---|---|---|---|
| | 0 | 1 | 2 | 3 | 4 | 5 | 6 | 7 | 8 | 9 | 10 |
| Controls: | | | | | | | | | | | |
| 5 | 0 | 0 | 0 | 0 | 0 | —* | 0 | — | 0 | 0 | 0 |
| 8 | 0 | 0 | 0 | 0 | 0 | — | 0 | 0 | 0 | 0 | 0 |
| 9 | 0 | — | 0 | 0 | 0 | — | — | 50 | 0 | — | 0 |
| 22 | 0 | — | — | 0 | 0 | 0 | 0 | 0 | 0 | 0 | — |
| 40 | 0 | 0 | 0 | 0 | 0 | 0 | 0 | — | 0 | 0 | 0 |
| 41 | 0 | — | 0 | 0 | 0 | — | 0 | 0 | 0 | 0 | 0 |
| 88 | 0 | — | 42 | 0 | 0 | 0 | 0 | 0 | 0 | 0 | 0 |
| 91 | 0 | 0 | 0 | 0 | — | 0 | — | — | 0 | 0 | 0 |
| ** | 0/8 | 0.4 | 1/7 | 0/8 | 0/7 | 0/4 | 0/6 | 1/5 | 0/8 | 0/7 | 0/7 |
| Vaccinates: | | | | | | | | | | | |
| 1 | 0 | 0 | 0 | 62 | 400 | 200 | 0 | 55 | 32 | 0 | 490 |
| 10 | 0 | 0 | 0 | 49 | 420 | 200 | 160 | 400 | 2000 | 33 | 0 |
| 12 | 0 | 23 | 42 | — | 46 | 200 | 0 | 33 | 32 | 100 | 320 |
| 50 | 0 | 62 | 0 | 20 | 500 | 230 | 160 | 49 | 110 | 0 | 0 |
| 79 | 0 | 0 | — | 80 | 110 | 150 | 370 | 270 | 1100 | 20 | 0 |
| 82 | 0 | — | 0 | 62 | 34 | 0 | 31 | 52 | 290 | 680 | 38 |
| 85 | 20 | 62 | 0 | 35 | 140 | 0 | 78 | 20 | 2000 | 700 | 440 |
| 93 | 0 | — | 0 | 250 | 450 | 120 | 200 | 44 | 44 | 0 | 0 |
| ** | 1/8 | 3/6 | 1/7 | 7/7 | 8/8 | 6/8 | 6/8 | 8/8 | 8/8 | 5/8 | 4/8 |

*Quantity of nasal secretions insufficient for testing.
**Number of calves with interferon/number of calves tested.

All nasal secretion samples were dialyzed in a KCl-HCl buffer (ph 2.0) overnight, and then a PBS buffer (ph 7.4) overnight before assay by plaque reduction. The plaque reduction method, as modified by Rosenquist and Loan (Am J Vet Res 28:619-628, 1967), was used. Serial dilutions of the prepared sample were made in maintenance medium. Two ml amounts of these dilutions were applied to 6 well petri dish cultures of bovine fetal kidney cells, and allowed to remain overnight at 37° C. Control cultures were treated overnight with 2 ml of maintenance medium. After the incubation period, fluids were aspirated, plates were washed with 2 ml of Hanks' BSS, and 0.25 ml of VSV (calculated to contain 50 PFU) was added to each petri dish. After adsorption at 37° C. for 1 hour, excess viral fluids were aspirated, and the overlay medium was added. Plaques were usually scored on the third day. Interferon titers were determined by the probit method (Lindenman and Gifford, Virology 19:302-309, 1963) and were expressed as the reciprocals of the dilutions which produced 50% reduction in the number of VSV plaques, as compared with the number in control cultures.

EXAMPLE 10

The source of interferon in this study was nasal secretions induced by vaccination with a number of vaccines for infectious bovine rhinotracheitis (IBR). The feed consumption for all calves including 10 control calves used in this study was studied for four days prior to vaccination. Each calf in its vaccination group was allowed to eat from one of five pinpointers. Data on this observation of feed consumption in the calves is shown in Table L.

TABLE L
Food Consumed in Pounds, Total 4-Day Consumption Before Trial

| Calf No. | Pinpointer Number | | | | |
|---|---|---|---|---|---|
| | 1 | 2 | 4 | 6 | 8 |
| 1 | 40 | 64 | 66 | 45 | 72 |
| 2 | 60 | 60 | 56 | 54 | 67 |
| 3 | 59 | 41 | 50 | 46 | 26 |
| 4 | 48 | 56 | 49 | 44 | 00 |
| 5 | 14 | 54 | 42 | NA* | 35 |
| 6 | 42 | 46 | 61 | 00 | 45 |
| 7 | 66 | 74 | 71 | 32 | 55 |
| 8 | 36 | 60 | 06 | 24 | 47 |
| 9 | 32 | BL** | 64 | 42 | 34 |
| 10 | 43 | 00 | 38 | 71 | 31 |
| Total | 440 | 455 | 503 | 358 | 412 |

TABLE L-continued

| | Food Consumed in Pounds. Total 4-Day Consumption Before Trial | | | | |
|---|---|---|---|---|---|
| | Pinpointer Number | | | | |
| Calf No. | 1 | 2 | 4 | 6 | 8 |
| Average | 44.0 | 50.6 | 50.3 | 39.8 | 41.2 |
| Avg. Daily Consumption | 11.00 | 12.64 | 12.58 | 9.94 | 10.30 |

*Calf substituted on day 0 from pen.
**Bloating calf dropped from study.

In addition to the control calves, ten calves vaccinated with the intranasal IBR vaccine TSV-2 in the same manner as described in Example 9 were studied. This trial also included nine calves vaccinated with an intramuscular (IM) IBR/PI-3 vaccine manufactured by Anchor Labs, ten calves vaccinated with a full dose of an intranasal IBR/PI-3 vaccine (Rhivin) manufactured by Pitman-Moore, Inc., and ten calves vaccinated with one tenth of a full dose of the Rhivin vaccine. The dose rates for each of these vaccine treatments is shown in Table H.

For each group of calves in the study, the total gain and average daily gains during the 60-day pretrial period are shown in Table M. Data collected before the trial indicated some differences in their pretrial performance as shown in Tables L and M. Though the groups were not identical, the data do reflect that the treatment groups were balanced and provided fair comparisons.

TABLE M

| | Pretrial Data on Weights and Weight Gain | | | | | | | |
|---|---|---|---|---|---|---|---|---|
| | No. of | 60-Day | 0-Day | Total Gain | | Average Daily Gain | | |
| Treatment | Calves | Weight | Weight | Pretrial | Posttrial | Pretrial | Posttrial | Change |
| Control | 10 | 415.8 | 567.4 | 151.6 | 64.4 | 2.53 | 2.30 | −0.23 |
| Anchor Labs (IM) | 9 | 420.2 | 564.1 | 143.9 | 69.0 | 2.40 | 2.46 | +0.06 |
| TSV-2 | 10 | 423.6 | 576.0 | 152.4 | 73.9 | 2.54 | 2.64 | +0.10 |
| RHIVIN | 10 | 416.0 | 565.9 | 149.9 | 67.5 | 2.50 | 2.41 | −0.09 |
| RHIVIN/10 | 10 | 415.6 | 572.2 | 156.6 | 69.5 | 2.61 | 2.48 | −0.13 |

Summary data for the trial following the specific treatments is presented in Table N. The calves treated with the TSV-2 intranasal vaccine demonstrated the greatest total gain, the best average daily gain, and the best efficiency of feed utilization.

TABLE N

| | | Summary Weights, Gains, Feed Consumption | | | | | |
|---|---|---|---|---|---|---|---|
| | | Average Weight* | | Average Total | Percent | Average Daily | Average Daily Feed | Feed/ |
| Pen | Treatment | Begin | End | Gain | Increase | Gain | Consumed | Gain** |
| 1 | Control**** | 567.4 | 631.8 | 64.4 | 11.4 | 2.30 | 15.14 | 6.58 |
| 2 | Anchor Labs (IM)*** | 564.1 | 633.1 | 69.0 | 12.2 | 2.46 | 15.41 | 6.26 |
| 4 | TSV-2 | 576.0 | 649.9 | 73.9 | 12.8 | 2.64 | 15.89 | 6.02 |
| 6 | RHIVIN | 565.9 | 633.4 | 67.5 | 11.9 | 2.41 | 15.20 | 6.31 |
| 8 | RHIVIN/10 | 572.2 | 641.7 | 69.5 | 12.1 | 2.48 | 16.34 | 6.59 |

*Beginning weight = average of 2 weights taken at 0 and 2 days. Ending weight = average of 2 weights taken at 28 and 29 days.
**Feed/gain calculated by dividing the average daily pounds of food consumed by the average daily gain.
***One calf removed from data of pen 2 because of bloating.
****Control calves seroconverted to IBR virus by 28 days indicating an inapparent IBR virus infection.

EXAMPLE 11

The effect of intranasal secretion interferon was tested in another study involving six bulls and six steers for each test group. One group was treated as a control, one group was vaccinated with the intranasal IBR vaccine TSV-2 in the same manner as in Example 9, and one group was vaccinated with the intramuscular IBR/PI-3 vaccine in the same manner as in Example 10.

Table O shows the beginning average weight and the average weight gains per calf at 7, 14, 21, 28, and 58 days following vaccination. Table P presents the average daily weight gain and the average weight gain as a percent of body weight at 28 and 58 days. The vaccinated calves averaged greater daily weight gain, with all calves treated with the TSV-2 intranasal vaccine showing the greatest average daily weight gain.

TABLE O

| | | Average weight gains for calves vaccinated with IBR vaccine | | | | | |
|---|---|---|---|---|---|---|---|
| | | | Average Gain | | | | |
| Pen* | Treatment | Average Weight | 7-Day | 14-Day | 21-Day | 28-Day | 58-Day |
| 25 | Bulls Control | 539.3 | 30.3 | 48.3 | 56.7 | 87.3 | 205.3 |
| 26 | Steers Control | 581.3 | 40.7 | 42.7 | 73.7 | 95.5 | 206.0 |
| 27 | Bulls IM | 541.8 | 24.8 | 43.8 | 58.2 | 111.3 | 245.7 |
| 28 | Steers IM | 596.2 | 16.2 | 27.8 | 67.2 | 94.5 | 210.7 |
| 29 | Bulls TSV-2 | 540.3 | 29.3 | 43.0 | 74.0 | 103.2 | 223.5 |
| 30 | Steers TSV-2 | 602.7 | 39.0 | 41.7 | 76.0 | 115.8 | 238.7 |

*Six calves per pen.

TABLE P

| | Average Daily Gains for Each Test Group | | | |
|---|---|---|---|---|
| | Average Daily Gain | | Gain as % Body Weight | |
| Treatment | 28-Day | 58-Day | 28-Day | 58-Day |
| Controls | 3.26 | 3.55 | 16.3 | 36.7 |
| IM | 3.68 | 3.93 | 18.1 | 40.1 |
| TSV-2 | 3.91 | 3.98 | 19.2 | 40.4 |

EXAMPLE 12

The effect of bovine fibroblast IFN on the appetite of litter-mate piglets was examined. Seventy piglets were selected at birth for the test, with thirty-five piglets serving as controls. Each of the thirty-five piglets chosen to receive IFN treatment was orally administered 5 ml of a bovine IFN material with a titer of 7000 units/ml. The interferon was given on each of the three days before weaning. The weights of the piglets as monitored is shown in Table Q. The litter-mate piglets differed in weight by only about 0.1 lb/pig at 21 days old, but 38 days after weaning, the IFN-treated pigs outweighed the controls by 1.5 lbs.

TABLE Q

| No. of Pigs | Treatment | Effect of Bovine IFN on Weight of 70 Pigs | | | | | | | |
|---|---|---|---|---|---|---|---|---|---|
| | | Weight (lbs.) at Day | | | | | | | |
| | | Birth | 10 | 21 | 28 | Weaning | W + 3 | W + 10 | W + 38 |
| 35 | IFN | 3.6 | 7.0 | 11.1 | 12.8 | 13.6 | 14.5 | 17.0 | 48.4 |
| 35 | Controls | 3.7 | 7.2 | 11.0 | 13.0 | 13.4 | 14.0 | 16.2 | 46.9 |
| | Benefit to IFN | −0.1 | −0.2 | +0.1 | −0.2 | +0.2 | +0.5 | +0.8 | +1.5 |

EXAMPLE 14

Another study of the effect of bovine IFN on the weight gain of litter-mate piglets was conducted. Seventy-two piglets were used in the trial, thirty-six receiving interferon treatment with the remainder serving as controls. The IFN-treated pigs were each given 7 ml of bovine IFN with a titer of 7000 units/ml. The IFN was orally administered on each of the three days prior to weaning. The weights of the piglets are presented in Table R. Though the litter-mate piglets differed in weight by an average of only about 0.13 lb at 21 days old, the IFN-treated pigs outweighed the controls by an average of 1.70 lbs at 38 days after weaning.

TABLE R

| No. of Pigs | Treatment | Effect of Bovine IFN on Weight of 72 Pigs | | | | | | |
|---|---|---|---|---|---|---|---|---|
| | | Weight (lbs.) at Day | | | | | | |
| | | Birth | 10 | 21 | Weaning | W + 3 | W + 10 | W + 38 |
| 36 | IFN | 3.7 | 7.1 | 11.40 | 14.40 | 15.05 | 18.06 | 41.72 |
| 36 | Controls | 3.7 | 6.9 | 11.27 | 14.23 | 14.80 | 17.54 | 40.02 |
| | Benefit to IFN | 0.0 | +0.2 | +0.13 | +0.17 | +0.25 | +0.52 | +1.70 |

The foregoing description has been directed to particular embodiments of the invention in accordance with the requirements of the Patent Statutes for the purposes of illustration and explanation. It will be apparent, however, to those skilled in this art that many modifications and changes in the apparatus and procedure set forth will be possible without departing from the scope and spirit of the invention. It is intended that the following claims be interpreted to embrace all such modifications and changes.

What is claimed is:

1. A method for increasing efficiency of food utilization of a warm-blooded vertebrate comprising administration to the warm-blooded vertebrate of a biologically active interferon in an amount effective to increase the efficiency in utilizing food for the warm-blooded vertebrate.

2. The method of claim 1 wherein the warm-blooded vertebrate is a mammal.

3. The method of claim 1 wherein the warm-blooded vertebrate is a bird.

4. The method of claim 1, 2, or 3 wherein the interferon is isolated from cells of bovine species origin.

5. The method of claim 4 wherein the interferon is fibroblast interferon.

6. A method for stimulating the appetite of cattle comprising administration to cattle an effective amount of a biologically active interferon found in cells of bovine species origin.

7. The method of claim 6 wherein the interferon is fibroblast interferon.

8. The method of claim 7 wherein each bovine is orally administered at least one dose of at least 10,000 units of bovine fibroblast interferon per kg of body weight.

9. The method of claim 7 wherein each bovine is intravenously administered daily for at least three days at least one dose of at least 4,000 units of bovine fibroblast interferon per kg of body weight.

10. A method for stimulating the appetite of cattle comprising inoculation of a bovine with a vaccinal virus strain in an amount effective to cause nasal secretion by the bovine of a biologically active interferon.

11. The method of claim 10 wherein the vaccinal virus strain is a vaccinal strain of infectious bovine rhinotracheitis virus.

12. The method of claim 11 wherein each bovine is inoculated with at least about $10^4$ TCID$_{50}$ of such vaccinal strain.

13. A method for stimulating the appetite of swine comprising administration to swine an effective amount of a biologically active interferon found in cells of bovine species origin.

14. The method of claim 13 wherein the interferon is fibroblast interferon.

15. The method of claim 14 wherein the swine are piglets prior to weaning and the piglets are orally administered about 5,000 to about 50,000 units of bovine fibroblast interferon per kg of body weight per day for from one to five days before weaning.

16. A method for increasing the efficiency of food utilization in chickens comprising administration to chickens an effective amount of a biologically active interferon found in cells of bovine species origin.

17. The method of claim 16 wherein the interferon is fibroblast interferon.

18. The method of claim 17 wherein the chickens receive the bovine fibroblast interferon in their drinking water in an amount of from about 70 units to about 7,000 units per ml of drinking water.

* * * * *